United States Patent [19]
Stickley

[11] Patent Number: 6,023,800
[45] Date of Patent: Feb. 15, 2000

[54] REMOVABLE ACCESSORY FOR A SURGICAL TABLE

[75] Inventor: Keith A. Stickley, Greenville, Ohio

[73] Assignee: Midmark Corporation, Versailles, Ohio

[21] Appl. No.: 08/853,629

[22] Filed: May 9, 1997

[51] Int. Cl.⁷ .................................................. A61G 13/10
[52] U.S. Cl. .................................. 5/621; 5/503.1; 5/658; 248/229.26
[58] Field of Search ................................ 5/621, 623, 624, 5/424, 508.1, 507.1, 658; 248/229.26, 228.6, 229.15

[56] References Cited

U.S. PATENT DOCUMENTS

| 2,607,401 | 8/1952 | Pruyne | 5/503.1 |
|---|---|---|---|
| 2,614,558 | 10/1952 | Lovell | 5/623 X |
| 2,678,792 | 5/1954 | Gallion et al. | 5/503.1 X |
| 2,876,359 | 3/1959 | Plymale | 250/58 |
| 3,046,072 | 7/1962 | Douglass Jr. et al. | 5/623 X |
| 3,065,344 | 11/1962 | Chervenka | 250/58 |
| 3,771,782 | 11/1973 | Anderegg | 269/322 |
| 3,952,481 | 4/1976 | Albertson | 248/228.6 |
| 3,997,792 | 12/1976 | Conrad et al. | 250/444 |
| 4,373,639 | 2/1983 | Tricon | 211/86 |
| 4,457,502 | 7/1984 | Beach | 269/11 |
| 4,852,841 | 8/1989 | Sebring | 248/231.5 |
| 4,901,963 | 2/1990 | Yoder | 248/231.5 |
| 4,901,964 | 2/1990 | McConnell | 248/231.5 |
| 5,077,780 | 12/1991 | Lee, Jr. | 378/196 |
| 5,135,210 | 8/1992 | Michelson | 5/658 |
| 5,174,533 | 12/1992 | Pryor et al. | 248/288.5 |
| 5,326,059 | 7/1994 | Pryor et al. | 248/231.7 |
| 5,400,772 | 3/1995 | LeVahn et al. | 5/503.1 X |

Primary Examiner—Michael F. Trettel
Attorney, Agent, or Firm—Biebel & French

[57] ABSTRACT

A removable accessory for use with a surgical table top having a generally planar top surface for supporting a patient. The accessory may be in the form of a detachable siderail which may be clamped onto the side edge of a surgical table top. The removable accessory includes an elongated clamp body defined by a C-shaped channel member having top and bottom legs connected by a connector portion. A clamp bar is supported on the bottom leg and is moved into engagement with a bottom surface of the surgical table top to thereby cause the accessory to be clamped to the table top. The table top is provided with a ridge along an upper edge thereof for positioning within a recess in the top leg of the clamp body for preventing the accessory from slipping off the edge of the table top.

12 Claims, 5 Drawing Sheets

REMOVABLE ACCESSORY FOR A SURGICAL TABLE

BACKGROUND OF THE INVENTION

1. Field of the Invention

The present invention relates to an accessory for use with a surgical table and, more particularly, to an accessory which may be easily clamped directly to the edge of a surgical table top whereby the accessory may be selectively positioned to a desired location on the table top or removed entirely from the table top.

2. Related Prior Art

Many medical procedures performed on a surgical table require that attachments or accessories be supported adjacent to the side of the table. For example, a procedure performed on a patient's arm may require that an arm board be supported and extend laterally from the side of a surgical table to support the patient's arm in an extended position. Similarly, a leg support may be required for supporting a patient's legs in a predetermined position to facilitate other surgical procedures. Alternatively, other attachments or accessories may be supported along the side of the table to meet the particular needs of the operating personnel.

Prior art surgical tables are typically constructed with siderails permanently attached along the opposing edges of the tables. The siderails are in the form of rectangular rails spaced laterally from the side edges of the table by spacers. Accordingly, accessories may be clamped onto the rails at desired locations along the table, depending on the requirements of the operation.

One difficulty associated with conventional siderails, relates to the performance of x-ray procedures which may be performed in the course of an operation. While it is known to form surgical tables of x-ray transparent material, such as composite materials, siderails along the sides of the tables form an obstruction to x-rays. For example, if it is desired to take an x-ray at an angle relative to the horizontal and vertical, the siderails may fall within the path of the x-ray image. Thus, an x-ray apparatus mounted on a conventional C-arm for taking x-rays at different angles may be limited, even when used with an x-ray transparent table.

A further difficulty associated with conventional siderails relates to access of the operating personnel to a patient. As a result of the conventional construction of providing siderails fixed in laterally spaced relation to the side edges of the surgical table, a surgeon is prevented from standing directly adjacent to the side edge of the surgical table. It is generally desirable to allow a surgeon to be positioned as close as possible to a patient in order to improve access to the area of surgery, as well as to reduce the fatigue to the surgeon during the medical procedure.

Accordingly, there is a need for an apparatus whereby accessories may be conveniently mounted to the side of a surgical table which does not obstruct the performance of x-ray procedures. In addition, there is a need for such an apparatus which facilitates access of a surgeon to a patient lying on a surgical table.

SUMMARY OF THE INVENTION

The present invention provides a removable accessory for use in combination with a surgical table top having a generally planar top surface and an opposing bottom surface, and substantially vertical side edges extending between the top and bottom surfaces. The accessory is adapted to be removably attached along any one of the side edges of the table top.

The removable accessory generally includes an elongated clamp body defined by a C-shaped channel member having generally parallel top and bottom legs. The top and bottom legs are connected by a connector portion wherein the top and bottom legs extend laterally from one side of the connector portion. A surgical table accessory is attached to the connector portion and is located on a lateral side of the connector portion opposite from the top and bottom legs.

The removable accessory is attached to a surgical table top by attachment means supported on the bottom leg and including a portion extending between the bottom leg and the top leg for engaging a bottom surface of the surgical table top whereby the top leg is biased into engagement with the top surface of the surgical table top. The attachment means preferably includes a clamp bar supported in spaced relation to the bottom leg by a pair of threaded members. The threaded members are threadably engaged with the bottom leg and include an end rotatably affixed to the clamp bar.

The surgical table top is preferably formed with ridges protruding upwardly from the top surface of the table along the side edges thereof. The top leg includes an inner surface which defines a recess for receiving a ridge along a side edge of the table. Cooperation between the recess and the ridge facilitates firm engagement between the removable accessory and the table top and acts to resist moment forces tending to rotate the removable accessory downwardly off the table top.

In the preferred embodiment, the accessory includes a siderail attached to the connector portion and laterally spaced from the connector portion by spacers. The accessory may be easily clamped to the table top for use, and removed when it is desired to have the side edge of the table top cleared for x-rays or other surgical procedures not requiring the presence of the accessory.

Accordingly, it is an object of the present invention to provide a surgical table accessory which may be directly attached to the side edge of a surgical table top.

It is a further object of the invention to provide an accessory for attachment to a surgical table top which may be attached to any desired location along the side edge of the table top.

It is yet another object of the invention to provide an accessory in combination with a surgical table top wherein the accessory and table top cooperate to permit the accessory to be firmly attached to the table top for use.

Other objects and advantages of the invention will be apparent from the following description, the accompanying drawings and the appended claims.

DETAILED DESCRIPTION OF THE PREFERRED EMBODIMENT

Figure 1:
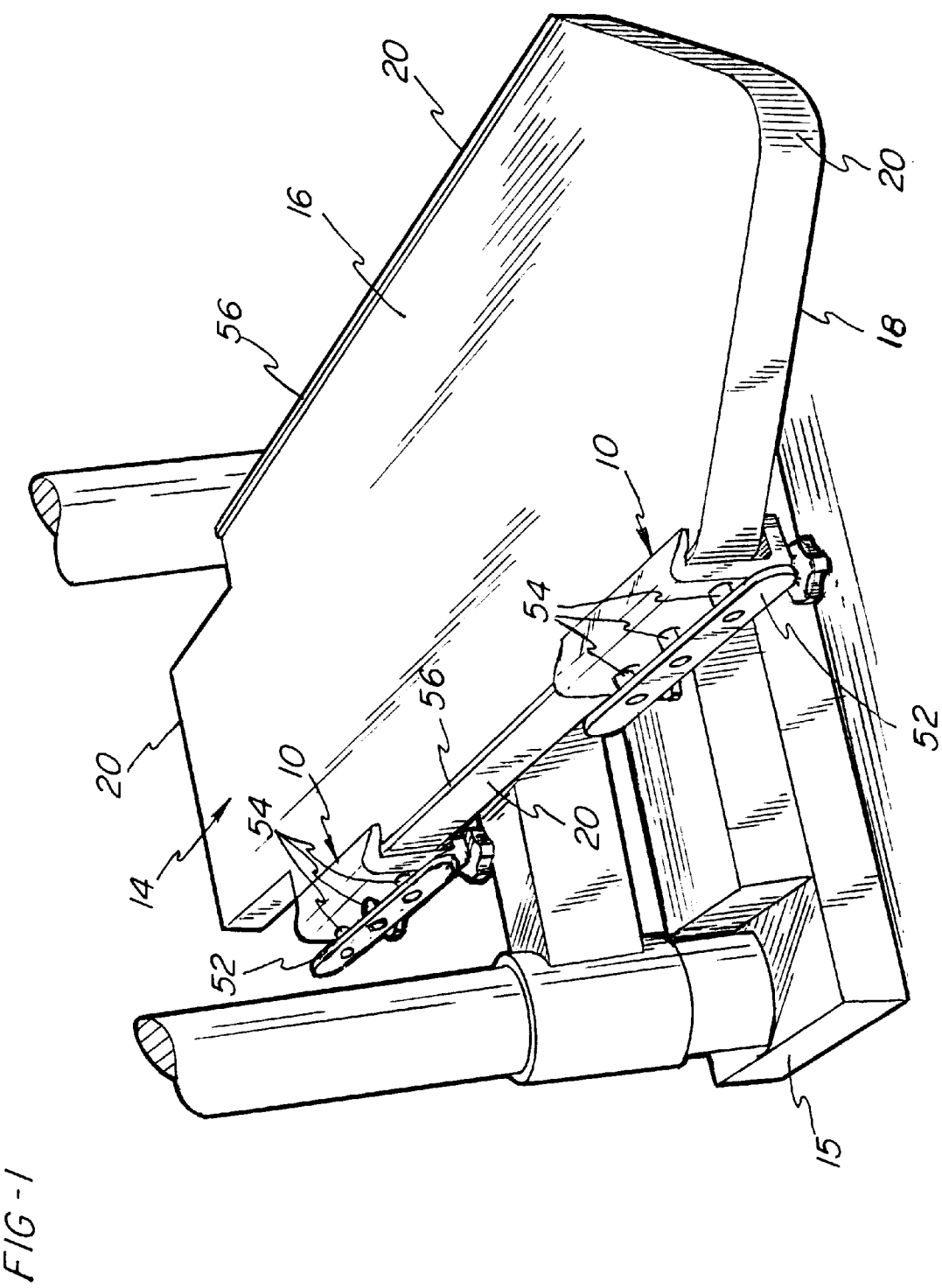
FIG. 1 is a perspective view showing two of the removable accessories of the present invention attached to a surgical table top configured to receive such accessories.

Referring to FIG. 1, the present invention is illustrated by removable accessory 10 attached to a surgical table top 14, which is supported on a base 15. As will be discussed further below the table top 14 is preferably specially configured to receive the accessory 10 of the present invention. The table top 14 is preferably formed of an x-ray transparent composite material, such as carbon fiber, and is provided with a substantially planar patient support top surface 16 and an opposing bottom surface 18, and substantially vertical side edges 20 extending between the top and bottom surfaces 16, 18.

Figure 2:
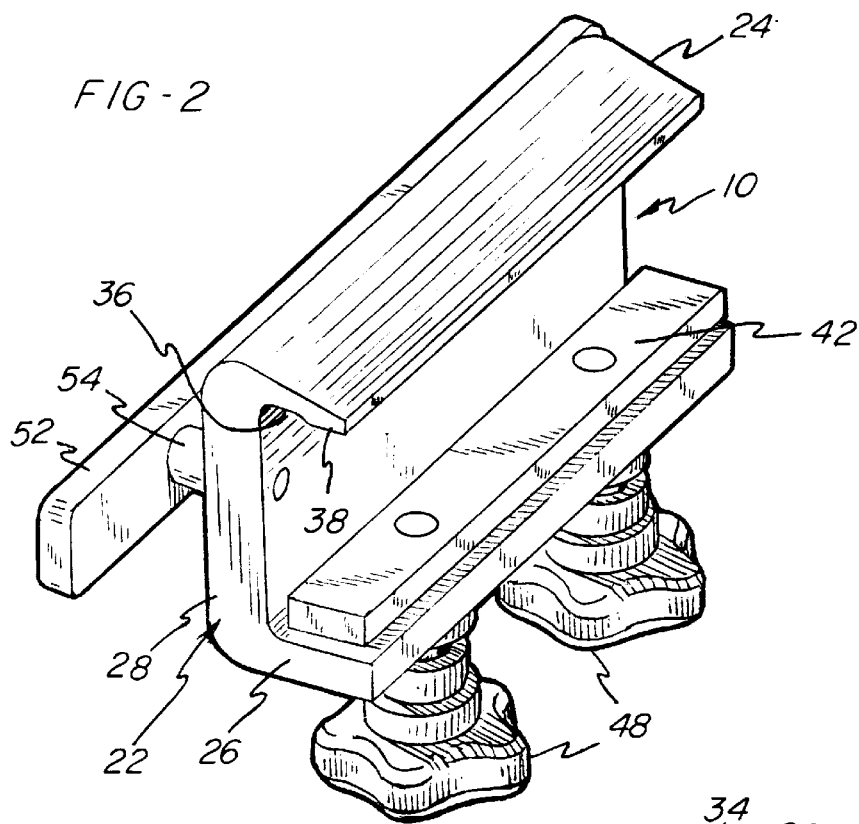
FIG. 2 is a perspective view of a removable siderail accessory.
Figure 3:
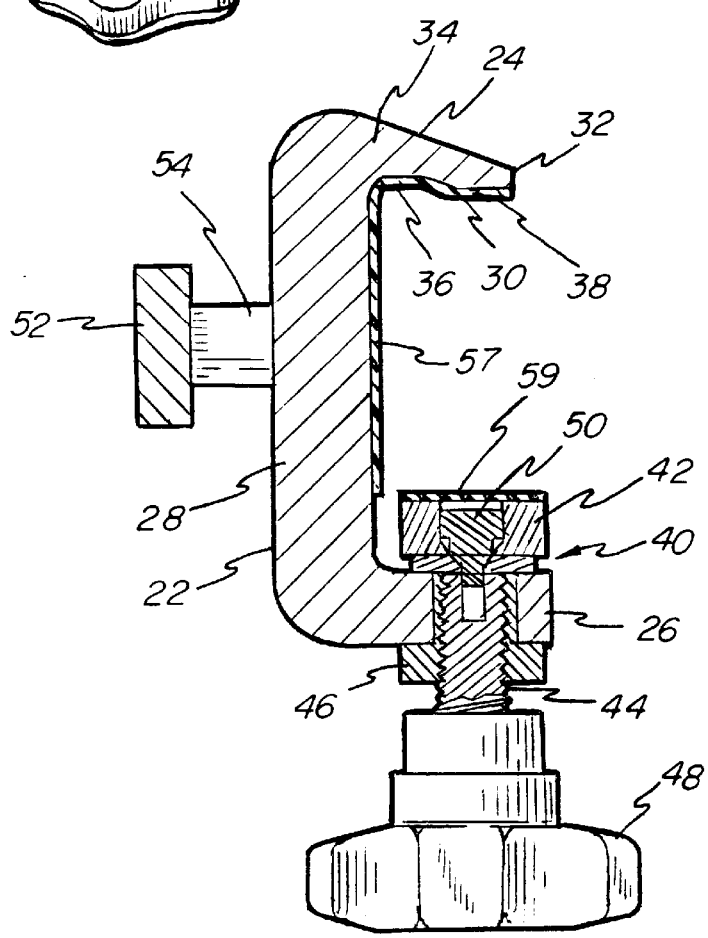
FIG. 3 is an end view of the siderail accessory of FIG. 2 shown in partial cross-section.
Figure 4:
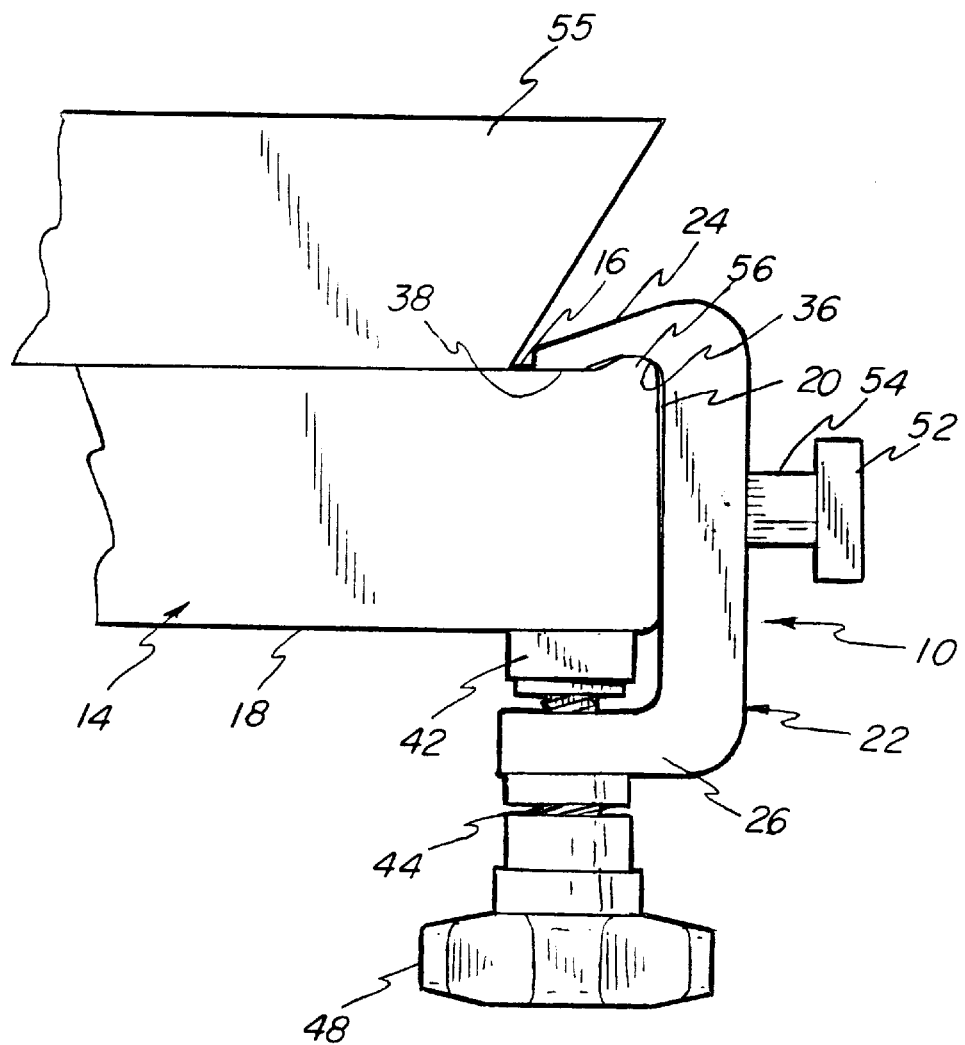
FIG. 4 is an elevational view of the siderail accessory of FIG. 2 mounted to a surgical table top configured to receive the accessory.

Referring further to FIGS. 2–4, the invention is described in detail with respect to the removable accessory 10 which comprises a siderail accessory adapted to be clamped onto the edge of the table top 14. The accessory 10 includes an elongated clamp body 22 which is defined by a C-shaped channel member. The clamp body 22 includes substantially horizontal top and bottom legs 24, 26 extending laterally from one side of a vertical connector portion 28.

The top leg 24 includes an inner surface 30 facing toward the bottom leg 26 for engaging with the top surface 16 of the table top 14. The top leg 24 includes an end 32 distal from the connector portion 28, and an opposing end 34 proximal to the connector portion 28. The inner surface 30 of the top leg 24 includes an upwardly angled portion defining a recess 36 at the proximal end 34 of the top leg 24, and further includes a planar portion 38 at the distal end 32 of the top leg 24.

An attachment means 40 is supported on the bottom leg 26 for facilitating engagement of the accessory 10 with the table top 14. The attachment means 40 comprises a clamp bar 42 affixed to the ends of identical threaded members 44. The threaded members 44 are threadably engaged with the bottom leg 26 and form an actuator for moving the clamp bar 42 relative to the clamp body 22. In particular, the bottom leg 26 is provided with spacers 46 inserted in apertures through the bottom leg 26 and having a threaded interior for threadably cooperating with respective threaded members 44.

A hand knob 48 is rigidly attached to the end of each threaded member 44 for turning the threaded member 44 relative to the bottom leg 26 and thereby moving the clamp bar 42 toward and away from the top leg 24. In addition, the clamp bar 42 is attached to the upper ends of the threaded members 44 by a shoulder screw 50 which allows limited movement of the clamp bar 42 relative to the threaded members 44 whereby the clamp bar 42 may align itself relative to the bottom surface 18 of the table top 14.

A siderail 52 is supported on the connector portion 28 wherein the siderail 52 is of a conventional rectangular design for providing a mounting point for supporting accessories on the table top 14. The siderail 52 is supported by a plurality of spacers 54 in laterally spaced relation to a side of the connector portion 28 opposite from the top and bottom legs 24, 26.

Referring to FIG. 4, the removable accessory 10 is shown positioned on the side edge of the table top 14 adjacent to the edge of a patient support cushion 55. The table top 14 is formed with a ridge 56 extending upwardly from the plane of the upper surface 16 adjacent to the edges 20 of the table top 14. The ridge 56 is located within the recess 36 at the upper end of the clamp body 22. In this view, it can be seen that the clamp bar 42 is biased into engagement with the bottom surface 18 of the table top 14 by rotation and upward movement of the threaded member 44 and hand knob 48. Thus, the hand knob 48 and threaded member 44 act as actuation means for actuating the clamping of the removable accessory 10 relative to the table top 14. Further, it should be noted that as the clamp bar 42 is actuated into engagement with the bottom surface 18, the planar end portion 38 of the top leg 24 is biased into engagement with the top surface 16 adjacent to the ridge 56. Cooperation between the ridge 56 and the recess 36 of the clamp body 22 prevents the accessory 10 from slipping off the table top 14 when a moment force tending to rotate the siderail 52 downwardly is applied.

It should be apparent that the removable accessory 10 may be conveniently attached to and removed from the side edge of the table top 14. Further, the accessory 10 may either be slid onto the table top 14 from an end of the ridge 56 and longitudinally moved to a desired location, or alternatively may be "rolled" onto the table by initially placing the distal end 32 of the clamp body 22 on the top surface 16 and then rotating the clamp body 22 downwardly to position the clamp bar 42 underneath the bottom surface 18.

In order to facilitate sliding movement of the clamp body 22 along the edge of the table top 14, the inner surfaces of the connector portion 28 and top leg 24 may be provided with a covering of low friction material 57 such as a thin sheet of TEFLON. Also, the upper surface of the clamp bar 42 may be covered with a high friction material 59, such as silicone rubber, to facilitate firm engagement with the bottom surface 18 of the table top 14.

It should be noted that the threaded member 44 and knob 48 may be replaced with other actuation means for moving the clamp bar 42 into engagement with the bottom surface 18 of the table top 14. For example, a ratchet mechanism, over center mechanism or any other conventional actuation mechanism may be incorporated to perform the clamping operation.

Figure 5:
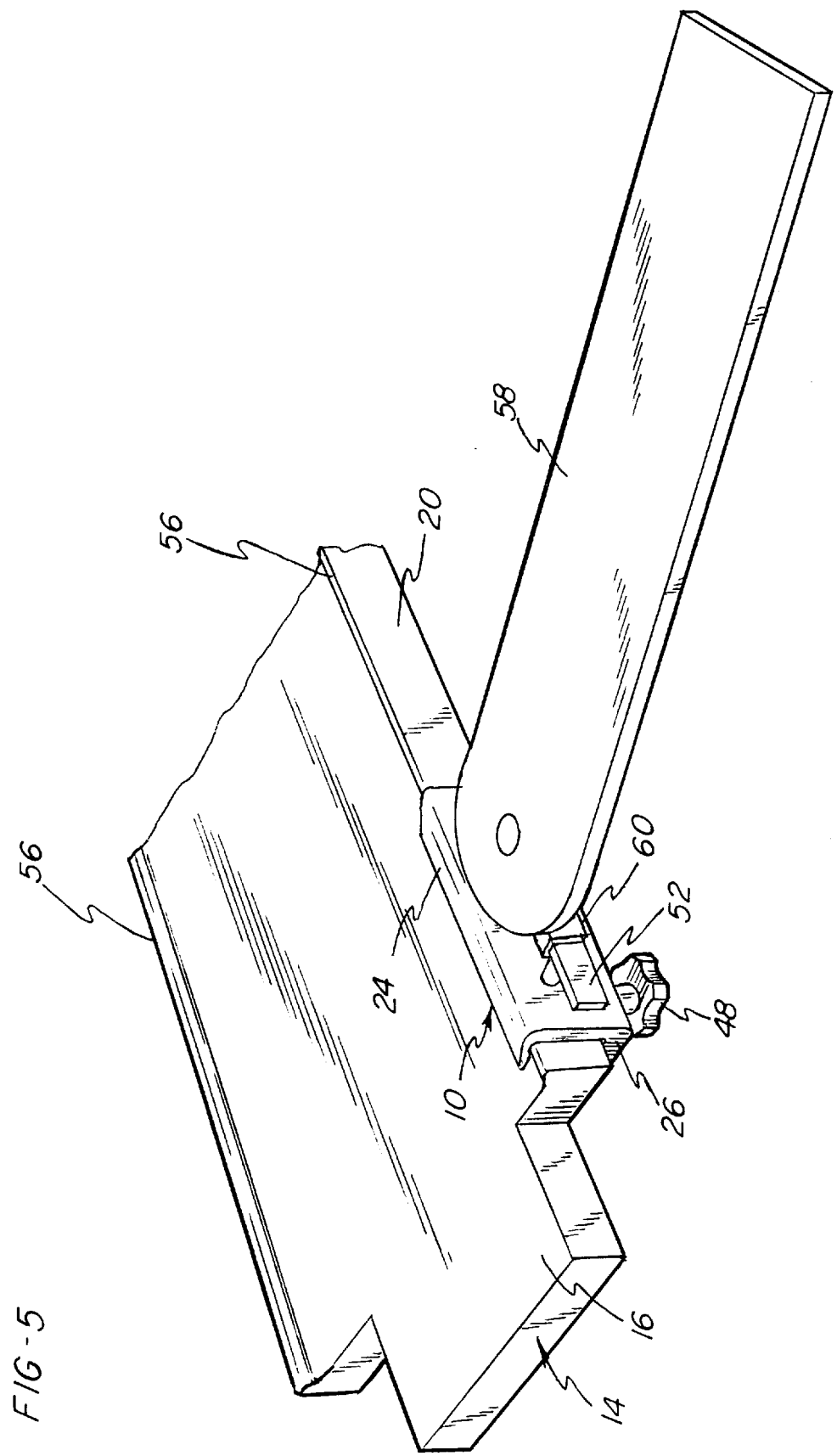
FIG. 5 is a perspective view illustrating the siderail accessory supporting an arm board.

Referring to FIG. 5, the siderail accessory 10 of the present invention is illustrated mounted on the edge of the table top 14 and supporting an arm board 58. The arm board 58 is supported on the siderail 52 in a conventional manner such as by means of a connector member 60 engaging around the siderail 52 and pivotally supporting the arm board 58.

Figure 6:
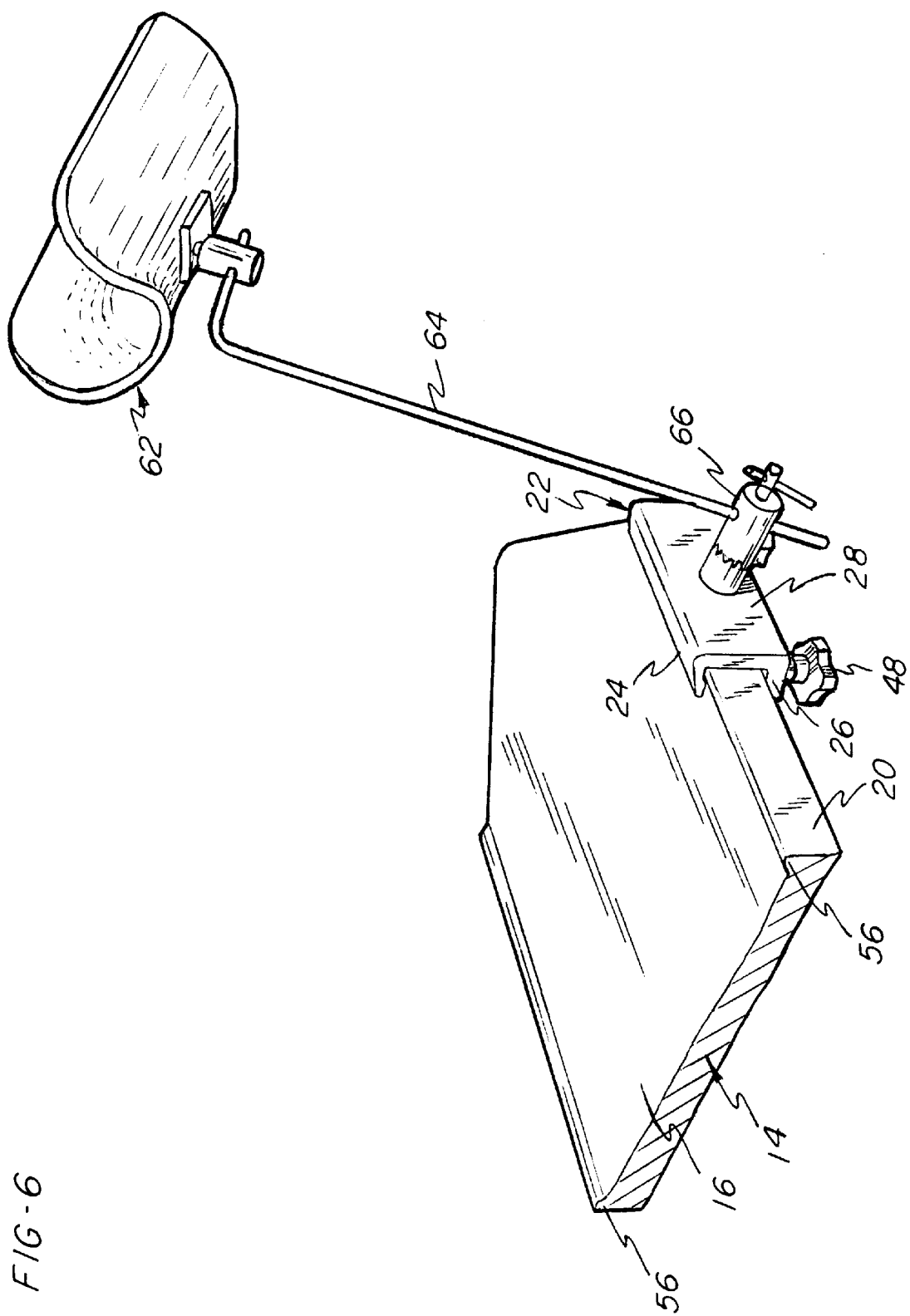
FIG. 6 is a perspective view showing an alternative accessory supported on a surgical table top.

FIG. 6 illustrates an alternative configuration for the present invention wherein the removable accessory comprises a leg support 62 supported via a rod member 64 to a rotatable socket 66. The socket 66 is shown attached directly to the connector portion 28 of the clamp body 22. Thus, the siderail 52 of the previous configuration has been replaced by the leg support 62 which is directly attached to the clamp body 22 and which is detachably mounted to the table top 14 in the same manner described above with regard to the siderail accessory.

From the above description, it should be apparent that the present invention provides a convenient means for detachably mounting a siderail or other accessory to the side of a table top. Further, it should be understood that although the ridges 56 are illustrated as being placed along the longitudinal edges of the surgical table top 14, additional ridges may be provided along the ends of the table top 14 for permitting accessories to be mounted at any desired location along the side edges of the table top 14. Further, it should be apparent that the present invention permits complete removal of the accessories from the side edge of the table top 14 for permitting a surgeon or other operating personnel to position themselves directly adjacent to the side edge of the table top during a surgical procedure.

A particular advantage associated with the present invention is the ability of operating personnel to operate an x-ray apparatus, such as an x-ray machine supported on a C-arm, without the inconvenience of the siderails being located along the side edges of the table top to block the procedure. Further, if it is necessary to immediately perform additional procedures, such as surgical procedures, accessories for facilitating the operation may be readily attached to the side edges of the table top in an efficient manner.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A removable accessory in combination with a surgical table top having a generally planar top surface and an opposing bottom surface, and side edges between said top and bottom surfaces, and removable accessory comprising:

an elongated clamp body defined by a C-shaped channel member having top and bottom legs connected by a connector portion, said top and bottom legs extending laterally from said connector portion;

a surgical table accessory attached to said connector portion and located to a lateral side of said connector portion opposite from said top and bottom legs;

attachment means supported on said bottom leg and including a portion extending between said bottom leg and said top leg and positioned in engagement with said bottom surface of said surgical table top to bias said top leg into engagement with said top surface of said surgical table top; and wherein said top leg includes an inner surface facing toward said bottom leg and an end of said top leg distal from said connector portion is located closer to said bottom leg than an end of said top leg proximate to said connector portion whereby a recess is defined by said inner surface, and said top surface of said surgical table top including an upwardly protruding ridge positioned in said recess.

2. The apparatus of claim 1 wherein said surgical table accessory comprises a siderail supported on said connector portion and located in laterally spaced relation to said connector portion and extending parallel to said side edges of said surgical table top.

3. The apparatus of claim 1 wherein said portion of said attachment means positioned in engagement with said bottom surface of said surgical table top comprises a clamp bar spaced from and extending generally parallel to said bottom leg.

4. The apparatus of claim 3 wherein said attachment means comprises actuation means movable relative to said bottom leg to move said clamp bar into and out of engagement with the bottom surface of said surgical table top.

5. The apparatus of claim 4 wherein said actuation means comprises a threaded member threadably engaged with said bottom leg and having an end rotatably affixed to said clamp bar.

6. The apparatus of claim 1 wherein said attachment means includes a threaded member threadably engaged with said bottom leg and having an end located between said top and bottom legs for movement toward and away from said top leg upon rotation of said threaded member.

7. The apparatus of claim 1 including a low friction material attached to said connector portion and to said top leg and positioned in engagement with one of said side edges and with said top surface of said surgical table top for sliding engagement.

8. The apparatus of claim 1 including a high friction material attached to said portion of said attachment means positioned in engagement with said bottom surface of said surgical table top for resisting movement between said attachment means and said surgical table top.

9. A removable siderail in combination with a surgical table top having a generally planar top surface and an opposing bottom surface, and substantially vertical side edges extending between said top and bottom surfaces, said removable siderail comprising:

an elongated clamp body extending longitudinally along one of said side edges of said surgical table top, said clamp body being defined by a C-shaped channel member having substantially horizontal top and bottom legs connected by a vertical connector portion, wherein said top and bottom legs extend over and below said top and bottom surfaces, respectively, and said connector portion extends along said one of said side edges of said surgical table top;

said top leg including an inner surface facing downwardly toward said top surface, and said inner surface including an upwardly angled portion defining a recess extending upwardly in an upper portion of said channel member;

a siderail supported on said connector portion and located in laterally spaced relation to said connector portion;

a clamp bar located between said bottom leg and said bottom surface; and actuation means supported on said bottom leg and biasing said clamp bar into engagement with said bottom surface, said actuation means being movable relative to said bottom leg to disengage said clamp bar from said bottom surface whereby said clamp siderail is removable from said surgical table top.

10. The apparatus of claim 9 including a ridge extending upwardly above said top surface and extending longitudinally along said at least one edge, said ridge being located in said recess in said upper portion of said channel member.

11. The apparatus of claim 9 wherein said actuation means comprises a threaded member threadably engaged with said bottom leg and having an end rotatably affixed to said clamp bar.

12. The apparatus of claim 9 including a sheet of low friction material attached to said connector portion and to said inner surface of said top leg for sliding engagement with said surgical table top, and a sheet of high friction material attached to said bar clamp for engaging and resisting movement relative to said bottom surface of said surgical table top.

* * * * *